United States Patent [19]

Muller et al.

[11] Patent Number: 5,320,731

[45] Date of Patent: Jun. 14, 1994

[54] IONTOPHORESIS DEVICE FOR TRANSCUTANEOUS ADMINISTRATION OF A GIVEN TOTAL QUANTITY OF AN ACTIVE PRINCIPLE TO A SUBJECT

[75] Inventors: Daniel Muller, Pau; Jean-Pierre Simonin, Paris, both of France

[73] Assignees: Societe Nationale Elf Aquitaine; Elf Sanofi, both of France

[21] Appl. No.: 16,888

[22] Filed: Feb. 12, 1993

[30] Foreign Application Priority Data

Feb. 14, 1992 [FR] France ............................ 92 01678

[51] Int. Cl.$^5$ ................................................ C25B 9/00
[52] U.S. Cl. .......................... 204/299 R; 204/180.1; 604/20
[58] Field of Search .................. 204/180.1, 299 R; 604/20

[56] References Cited

U.S. PATENT DOCUMENTS

| | | | |
|---|---|---|---|
| 4,167,190 | 9/1979 | Sorenson et al. | 128/423 |
| 4,474,570 | 10/1984 | Ariura et al. | 604/20 |
| 4,744,787 | 5/1988 | Phipps et al. | 604/20 |
| 4,747,819 | 5/1988 | Phipps et al. | 604/20 |
| 4,764,164 | 8/1988 | Sasaki | 604/20 |
| 4,927,408 | 5/1990 | Haak et al. | 604/20 |
| 5,047,007 | 9/1991 | McNichols et al. | 604/20 |
| 5,057,072 | 10/1991 | Phipps | 604/20 |
| 5,084,008 | 1/1992 | Phipps | 604/20 |
| 5,135,477 | 8/1992 | Untereker et al. | 604/20 |
| 5,162,043 | 11/1992 | Lew et al. | 604/20 |
| 5,203,768 | 4/1993 | Haak et al. | 604/20 |

FOREIGN PATENT DOCUMENTS

| | | |
|---|---|---|
| 2206493A | 1/1989 | United Kingdom . |
| WO91/16946 | 11/1991 | World Int. Prop. O. . |
| 9116944 | 11/1991 | World Int. Prop. O. . |

*Primary Examiner*—John Niebling
*Assistant Examiner*—C. Delacroix-Muirheid
*Attorney, Agent, or Firm*—Bacon & Thomas

[57] ABSTRACT

The iontophoresis device for transcutaneous administration of the active principle to the subject comprises electrodes, at least one of which is a consumable electrode formed of an electrochemically consumable material associated either with an insulating support or with a particular electronically conducting support. The single consumable electrode or one of the consumable electrodes holds a limited quantity of electrochemically consumable material, the said limited quantity being chosen so that the quantity of electricity necessary for its electrochemical consumption corresponds to the quantity of electricity necessary for administering the given total quantity of active principle to the subject and the active principle is present at the start of the operation in a quantity greater than the said given total quantity.

33 Claims, No Drawings

IONTOPHORESIS DEVICE FOR TRANSCUTANEOUS ADMINISTRATION OF A GIVEN TOTAL QUANTITY OF AN ACTIVE PRINCIPLE TO A SUBJECT

The invention relates to an iontophoresis device for transcutaneous administration of a given total quantity of an active principle to a subject.

In the current treatment of numerous diseases, it is necessary to administer a medication or other active principle to a subject in a controlled and often prolonged manner. Amongst the numerous techniques available to the formulation pharmacist, that of iontophoresis represents an advantageous alternative for controlling the administration of active principles such as medicinal substances into the body of the subject. One such technique consists in using an electric current for controlling the quantity but also the speed of delivery of an active principle through the skin of a subject. In numerous cases, this technique proves highly effective by significantly increasing the supply of active principle due to the current, in comparison to the quantity delivered without a current.

The transcutaneous administration of an active principle by iontophoresis to a subject is generally performed, starting with an aqueous solution or aqueous gel holding the active principle in an at least partially ionised form or in a neutral form, by applying an electric signal between, on the one hand, a first electrode called the active electrode, having the same polarity as the ions of the active principle to be administered or a positive polarity if the active principle is neutral, and being in contact with a reservoir element, which holds the active principle and is placed in contact with a first area of the skin of the subject, and, on the other hand, a second electrode called the back electrode or passive electrode, of opposite polarity to that associated with the active principle, which is placed, directly or via an indifferent electrolyte, in contact with a second area of the skin of the subject which is separate from the first area. During the passage of the current generated by applying a voltage between the electrodes, in the circuit thus produced, the ions of the active principle migrate away from the electrode of the same polarity (active electrode), through the skin and the tissues of the subject towards the electrode of opposite polarity(back or counter electrode)and thus find themselves passing through the circulatory system of the subject. In the same way, the active principle neutral molecules are entrained, away from the positive electrode, in the aqueous electroosmotic flux through the skin and the tissues of the subject towards the negative electrode (back electrode) and thus also find themselves passing through the circulatory system of the subject.

A known technique for administering a given total quantity of active principle by iontophoresis to a subject consists in operating by setting a current of constant intensity I and in stopping the treatment at the end of a time t such that the quantity of electricity $Q = I \times t$ corresponds to the theoretical quantity of electricity necessary for administering the given total quantity of active principle. In such a technique, maintaining the intensity of the current at a constant value may lead to a substantial variation in the electric voltage applied between the electrodes, because the impedance of the skin is not constant with time and may furthermore vary greatly from one individual to another and, for the same individual, from one area of administration of the active principle to another. This results in the appearance of phenomena of intolerance, burns, even destruction by oxidation or reduction of the active principle or principles to be administered with the formation of secondary compounds, as well as significant variations in pH which are often poorly tolerated. It is then necessary to add safety devices which limit the voltage in the electronic circuits used for generating the constant-intensity current in the iontophoresis circuit, the said devices, in addition to the extra cost which they entail, constitute an additional risk of breakdown or accident.

Another known technique for administering a given total quantity of active principle by iontophoresis to a subject consists in operating by setting a constant electric voltage between the electrodes and in continuously measuring the quantity of electricity used since the start of the treatment, and in stopping the said treatment when the said quantity of electricity reaches a value corresponding to that of the theoretical quantity of electricity necessary to administering the given total quantity of active principle. The major drawback of this technique resides in the fact that it is necessary to use a coulometer to measure the quantity of electricity used during the treatment, because the presence of such an apparatus complicates the structure of the electronic circuits of the iontophoresis device and makes the production of this device and its use more expensive. Furthermore, the use of a coulometer is ill-suited to the use of pulsed currents.

The present Applicants have observed that when, on the one hand, the medium holding the solution of active principle connected to the active electrode and the medium holding the indifferent electrolyte connected to the back electrode and, on the other hand, the electric signals applied to the iontophoresis systems are well-defined, the total quantities of active principles diffusing through the skin of a subject depend little on the current densities which are highly variable from one subject to another or from one treatment to another, but are directly related to the total quantity of current which has flowed between the electrodes. In other words, the electrical efficiency, that is to say the quantity of active principle which has diffused through the skin under the action of the same quantity of current, depends on the reaction media and on the signals applied between the electrodes but depends very little on the subjects. Using these observations, the present Applicants have found that a given total quantity of active principle could be administered very simply through the skin of a subject by iontophoresis by making up at least one of the electrodes of the iontophoretic system by a consumable electrode leading, after the passage of a predetermined quantity of current, either to a significant overpotential with respect to its initial state or alternatively to a break in the electrochemical chain employed so that the said current is practically broken.

By operating according to the invention, it is possible to administer given total quantities of active principle transcutaneously by iontophoresis to a subject without encountering the known drawbacks of the prior art mentioned hereinabove.

The subject of the invention is therefore an iontophoresis device for transcutaneous administration of a given total quantity of an active principle to a subject, the said device being of the type comprising a first electrode assembly consisting of a first electrode called the active electrode, in contact with a reservoir element, adapted, on the one hand, in order to contain an electrolyte holding the active principle in an at least partially ionised form or in a neutral form, and, on the other hand, in order to ensure, when it is placed in contact with an area of the skin of the subject, ionic conducting continuity between the said first electrode and the said area, the said first electrode having the same polarity as the ions of the active principle or a positive polarity if the active principle is neutral, a second electrode assembly consisting either (i) of a second electrode, called the back electrode, of opposite polarity to that associated with the active principle, or preferably (ii) of a second electrode of this type in contact with a receptor element holding an indifferent electrolyte, the said receptor element being arranged in order to ensure, when it is placed in contact with a portion of the skin of the subject, ionic conducting continuity between the second electrode and the said portion, and an electric signal generator connected to the two electrodes, the first electrode in contact with the reservoir element and/or the second electrode in contact with the receptor element being a consumable electrode formed of an electrochemically consumable material associated either with an insulating support, or with an electronically conducting support, the said electronically conducting support being made of a material which resists corrosion by the electrolyte associated with the electrode in the absence of a current and which has, when the consumable electrode is of the cathode type, a hydrogen overpotential in the presence of the said electrolyte at least equal to that of aluminium or alternatively which is not consumable by electrochemical oxidation when the consumable electrode is of the anode type, and being characterised in that the consumable electrode or one of the consumable electrodes holds a limited quantity of an electrochemically consumable material associated with the support, the said limited quantity being chosen so that the quantity of electricity necessary for its electrochemical consumption corresponds to the quantity of electricity necessary for administering the given total quantity of active principle to the subject, so that the flow of the current between the electrodes is practically broken when the consumable material of the electrode carrying the limited quantity of consumable material and called limiting consumable electrode, has been consumed, and in that the active principle is present in the reservoir element at the start of the operation in a quantity greater than the given total quantity to be administered to the subject.

If the reservoir element held, at the start of the operation, only a quantity of active principle equal to the given total quantity of active principle to be administered, and if the current was passed until this quantity had entirely diffused through the skin of the subject, the said current, towards the end of the operation, would act above all to transport ions other than those of the active principle, which would lead to excessive energy consumption and long treatment times. It is therefore preferable, in order to avoid the above drawbacks, for the quantity of active principle present in the reservoir element at the start of the operation to be in excess with respect to the said given total quantity, the said excess being able, for example, to be from approximately 2% to 1000% and more specifically from approximately 2% to 500% of this given total quantity.

The electrode, which is formed by the combination of the limited quantity of the electrochemically consumable material and of its support, namely an electronically conducting support having the aforementioned characteristics or alternatively an insulating support, and what is here termed the "limiting consumable electrode" may be used as the active electrode or as the back electrode, and may accordingly be of the anode type or alternatively of the cathode type. In either case, it is possible to use an active electrode of the limiting consumable electrode type associated with a back electrode which is not electrochemically consumable or alternatively to employ an active electrode which is not electrochemically consumable associated with a back electrode of the limiting consumable electrode type. It is also possible to use an active electrode and a back electrode which are both consumable electrodes, one of the said electrodes being a limiting consumable electrode, while the other electrode is a non-limiting consumable electrode. The term non-limiting consumable electrode is used to mean an electrode holding an electrochemically consumable material in a quantity in excess with respect to the quantity which would be consumed by the passage of the quantity of electricity consuming the quantity of electrochemically consumable material of the limiting consumable electrode.

In a consumable electrode of the cathode type, whether it is a limiting consumable electrode or a non-limiting consumable electrode, the electrochemically consumable material is consumed by reduction. It may advantageously be chosen from the ionisable metal compounds whose metal ions are capable of being electrochemically reduced into the corresponding metal. Among these metal compounds, mention may be made in a non-limiting manner of the compounds AgCl and CuCl.

In a consumable electrode of the anode type, whether it is a limiting consumable electrode or a non-limiting consumable electrode, the electrochemically consumable material is consumed by oxidation. It may be chosen from the metals which are consumed by electrochemical oxidation, and in particular from metals such as Al, Cu, Mg, Zn and Ag.

The support of the limiting consumable electrode may be made from an insulating material and in particular from an insulating organic plastic material such as polypropylene, polyethylene, PVC, polyamide or alternatively from a metal or non-metal electronically conducting material having the previously defined characteristics, the said electronically conducting material being able advantageously to be such as titanium, aluminium, silver, tantalum, vanadium, stainless steel, zinc, carbon, graphite or a conducting polymer, when the limiting consumable electrode is the cathode, or alternatively such as platinum, titanium, stainless steel, gold, carbon, graphite and a conducting polymer when the limiting electrode is the anode. The non-limiting consumable electrode may also have a structure comparable to that of the limiting consumable electrode and may therefore comprise a support as defined hereinabove.

By way of non-limiting examples of limiting consumable electrodes or of non-limiting consumable electrodes which are usable as cathodes in the device according to the invention, mention may be made of the electrodes based on AgCl or on CuCl on a silver, copper, stainless steel, titanium, carbon, polypropylene, polyethylene or conducting polymer support. As examples of limiting consumable electrodes or of non-limiting consumable electrodes which are usable as anodes in the device according to the invention, mention may be made, by way of non-limiting example, of the non-limiting electrodes based on a metal which is consumable by electrochemical oxidation chosen from Al, Ag, Cu, Mg and Zn and the limiting electrodes based on such a metal deposited on an insulating support such as polypropylene or polyethylene or on an electronically conducting support chosen from titanium, stainless steel, platinum, carbon, graphite and a conducting polymer.

As previously indicated, the electrochemically consumable material of the limiting consumable electrode is present in the said electrode in a quantity such that the quantity of electricity necessary for its electrochemical consumption corresponds to the quantity of electricity to be used for administering the given total quantity of the active principle to the subject. This latter quantity of electricity, which essentially depends on the iontophoretic system employed, that is to say on the reaction media in contact with the active electrode and the back electrode, on the electric signal applied to the electrodes and on the nature of the said electrodes, is determined through prior tests for each type of iontophoretic system used.

The electrodes which are not electrochemically consumable that can be used as active electrodes or as back electrodes in the device according to the invention can be chosen from among the electrodes which are not electrochemically consumable normally used in iontophoresis. In particular, electrodes made of carbon, platinum, titanium, stainless steel, graphite or a conducting polymer may be resorted to.

The electric generator applies between the active electrode and the back electrode an electric signal which can be either an intensiometric signal, that is to say a signal of set average intensity, which is for example constant (intensiostatic signal), or, preferably, a potentiometric signal, that is to say a signal of set average voltage, which is for example constant (potentiostatic signal). The electric signal of the intensiostatic type or of the potentiostatic type may be continuous or pulsed and permanent or intermittent, with or without temporary polarity inversion. Its frequency may be from 0 to 500 kHz and more particularly from 0 to 100 kHz. When the electric signal is of a pulsed type, it may have a duty ratio, that is to say a ratio between the duration of the elementary pulse, whose repetition forms the pulsed signal, and the time interval separating two successive appearances of this pulse, ranging from 0.05 to 0.95 and more particularly from 0.1 to 0.8.

Advantageously, the average voltage of the signal applied between the active electrode and the back electrode is chosen between 0.1 and 50 volts and more especially between 0.5 and 20 volts so that the density of the average current generated between the said electrodes has a value less than 5 mA/cm$^2$, more particularly less than or equal to 1 mA/cm$^2$, and for example between 0.03 and 0.5 mA/cm$^2$.

The electric signal generator of the device according to the invention can be of any known type allowing generation of electric signals of set average intensity or of set average voltage, which are continuous or pulsed and permanent or intermittent, with or without temporary polarity inversion, and which have the characteristics defined hereinabove.

The electrolyte, which is present in the reservoir element in contact with the active electrode, advantageously contains an aqueous solution or an aqueous gel, adhesive or otherwise, which holds the active principle to be administered in an at least partially ionised form or in a neutral form. In the same way, the indifferent electrolyte, which is possibly in contact with the back electrode, is, at least partially, in the form of an aqueous solution or of an aqueous gel which is adhesive or otherwise. These aqueous solutions or gels may constitute the whole of the electrolyte present in the reservoir element or of the indifferent electrolyte or alternatively may form only a part of the said electrolytes and then be dispersed in a non-aqueous medium forming the rest of the electrolyte and chosen so as not to break the ionic conducting continuity between the electrode and the skin and in order to increase the quality of the adhesion between the electrode and the skin. These aqueous solutions or aqueous gels may be obtained, as is well known in iontophoresis techniques. Examples of aqueous gels or of thick aqueous solutions are in particular respectively described in references U.S. Pat. No. 4,764,164 and U.S. Pat. No. 3,163,166.

The aqueous media holding the active principle, as well as the aqueous media constituting the indifferent electrolyte may hold, as is well known in iontophoresis, buffer agents capable of controlling the pH of the said media. It is possible further to control the pH of the said aqueous media without recourse to buffer agents, by using a reversible consumable electrode, which makes it possible to avoid or at least greatly to reduce the introduction of foreign ions into the skin from the aqueous media holding the active principle.

The iontophoresis device according to the invention allows transcutaneous administration to a subject of various active principles, and, in particular, therapeutic molecules such as, for example, insulin, metoprolol, hydrocodone, tetracyclines, salbutamol, valproic acid, propranolol, arginine-desmopressin, despopressin or others.

The device according to the invention may be produced starting with any known iontophoresis device, which has been modified in order to replace one of its electrodes, namely the active electrode or back electrode, by a limiting consumable electrode according to the invention, that is to say, as defined earlier.

In particular, the device according to the invention may be a portable self-contained device, to be fixed by a bracelet or possibly to be stuck onto the skin, comprising electrodes each having an area less than 50 cm$^2$ and more particularly between 1 and 40 cm$^2$ and a miniaturised electric signal generator. Thus, a self-contained portable device according to the invention can have a structure similar to those of self-contained portable iontophoresis devices described, for example, in the references U.S. Pat. Nos. 4,325,367, 4,557,723, EP-A-0,060,452 and FR-A-2,509,182 with the reservation that one of the electrodes of the said device is a limiting consumable electrode according to the invention, the said limiting and non-limiting electrodes each having an area less than 50 cm and more particularly between 1 and 40 cm$^2$. For example, use may be made of a limiting consumable electrode of the cathode type based on AgCl or on CuCl on a silver, copper, carbon, polypropylene, polyethylene or conducting polymer support, the non-limiting electrode, namely the anode, being able to be a conventional anode, for example an anode made of a metal or metal alloy such as titanium, Pt, stainless steel or alternatively from a nonmetallic electronically conducting material such as carbon or graphite or also a nonreversible or reversible consumable anode, for example an anode made of a metal such as Al, Cu, Mg, Zn and Ag possibly deposited on an insulating support such as polypropylene or polyethylene or alternatively on an electronically conducting support chosen from titanium, stainless steel, platinum, carbon, graphite and a conducting polymer. Use may also be made of a limiting consumable electrode of the anode type, for example, based on a metal chosen from Al, Ag, Cu, Mg and Zn deposited on a polypropylene, polyethylene, titanium, stainless steel, platinum, carbon, graphite or conducting polymer support, the non-limiting electrode, namely the cathode, being able to be a conventional cathode, for example a cathode made of carbon, graphite, titanium, stainless steel or a conducting polymer or alternatively a non-limiting consumable cathode, for example based on AgCl or CuCl on a silver, copper, carbon, polypropylene, polyethylene or conducting polymer support.

The invention is illustrated by the following examples which are given by way of non-limitation.

EXAMPLE 1

Study of the transdermic passage of fluorescein in the form of a sodium salt by iontophoresis.

The operations were carried out in iontophoresis cells of identical structure. Each iontophoresis cell consisted of two coaxial adjacent cylindrical compartments of 2 $cm^2$ cross-section, namely a donor compartment and a receiver compartment or back-electrode compartment, these two compartments being separated from each other, in a leaktight manner, by a piece of nude rat (OFA hr/hr) skin which is used as the membrane for the transcutaneous diffusion study. The donor compartment, with a volume of 3 ml, held an aqueous solution of 0.1% by weight of the sodium salt of fluorescein and was equipped with a magnetic bar allowing the solution to be homogenised. The receiver or back electrode compartment, identical to the donor compartment, held physiological salt solution with 500 ppm by weight of $NaN_3$ and was also agitated using a magnetic bar. At its end opposite the receiver compartment, the donor compartment was fitted with an electrode consisting of a previously chloridised silver film of 25 $\mu m$ thickness and of 2 $cm^2$ of active surface area.

This chloridisation was effected electrochemically by passing a direct current of 10 mA when the said silver film was immersed in a 0.1N hydrochloric acid bath and constituted the positive pole with respect to a copper electrode which was also immersed in the same HCl bath, the quantity of current being controlled, by means of a coulometer mounted in the circuit, in order to form the desired quantity of AgCl on the silver film. The back electrode compartment was fitted with a 2 $cm^2$ electrode of slightly chloridised silver (quantity of AgCl corresponding to 0.1 coulomb/$cm^2$). The chloridised face of each electrode being turned towards the rat-skin membrane side.

The samples of rat skin had all the subcutaneous tissue removed and had been preserved by freezing to −40° C. until they were mounted in the iontophoresis cell, with the dermal faces turned towards the receiver compartment, after having passed 15 minutes at room temperature in physiological salt solution with 0.05% by weight of $NaN_3$ added.

For each of the tests carried out, four identical iontophoresis cells (cells A, B, C and D) were started up simultaneously. The effective exchange surface was 2 $cm^2$ for each skin.

A pulsed current generator made it possible simultaneously to establish between the electrodes of the four cells mounted in parallel, an electric signal of the potentiometric type with peak voltage equal to 4 volts and with a duty ratio of 30% and a frequency of 20 kHz. A resistance of 100 ohms was connected in series in the circuit.

Following the voltage at the terminals of this resistor made it possible to determine the instant from which the silver chloride had been consumed completely, the said instant being indicated by a sudden drop in the said voltage.

The pulsed current generated by the generator was applied for 6 hours, the donor compartment of each cell containing the fluorescein being connected to the negative pole of the said generator and the back electrodes of the cells to the positive pole.

At the end of the said time, the medium contained in the receiver compartment was sampled, and the quantity of fluorescein which had passed through the skin separating the donor and receiver compartments of each cell was determined by fluorescence assay.

Five tests 1a to 1e were carried out as follows:

Test 1a : No current was applied to the electrodes, in order to determine the passive transcutaneous diffusion over 6 hours.

Test 1b : The silver chloride electrode present in the donor compartment held a quantity of AgCl corresponding to 20 coulombs, that is to say very much greater than the quantity capable of being consumed during the running time (6 hours) of the iontophoresis operation (non-limiting electrode).

Tests 1c to 1e : The silver chloride electrode present in the donor compartment held a quantity of AgCl corresponding respectively to 1 coulomb (test 1c), coulombs (test 1d) and 4 coulombs (test 1e), that is to say less than the quantity capable of being consumed during the running time (6 hours) of the iontophoresis operation (limiting electrode).

For each of the tests, the following were determined for each cell:

the total quantity Q of fluorescein which had diffused into the receiver compartment in 6 hours;

the length of activity of the electrode of the donor compartment, that is to say the length of operation of the iontophoresis in the case of tests 1a and 1b without a limiting electrode or alternatively the time at the end of which the silver chloride of the limiting electrode was consumed in the case of tests 1c to 1e with a limiting electrode;

the flux F representing the quantity Q divided by the length of activity and by the surface area of the electrode; and the ratio Q/n of the quantity Q to the quantity of silver chloride consumed, the latter quantity being expressed in coulombs.

The results obtained are given in Table I.

TABLE I

| | Cell A | Cell B | Cell C | Cell D | Mean | Standard deviation | % variation |
|---|---|---|---|---|---|---|---|
| Test 1a | Passive transcutaneous diffusion over 6 hours | | | | | | |
| Q ($\mu g$) | 0.5 | 1.2 | 0.2 | 1.4 | 0.82 | 0.49 | 50% |
| F ($\mu g$/$cm^2 \cdot h$) | 0.04 | 0.1 | 0.02 | 0.12 | 0.07 | 0.04 | 50% |
| Test 1b | Iontophoresis over 6 hours - non-limiting reversible electrodes | | | | | | |
| Q ($\mu g$) | 76.8 | 62 | 198.4 | 135.6 | 118.3 | 53.4 | 46% |
| F ($\mu g$)/ | 6.4 | 5.17 | 16.5 | 11.3 | 9.85 | 4.49 | 46% |

TABLE I-continued

| | Cell A | Cell B | Cell C | Cell D | Mean | Standard deviation | % variation |
|---|---|---|---|---|---|---|---|
| Test 1c | Iontophoresis over 6 hours - Ag/AgCl electrodes with 1 C of AgCl | | | | | | |
| Q (µg) | 15.55 | 20.1 | 16.75 | 19.7 | 18.02 | 2.1 | 10.7% |
| Length of activity (h) | 4.5 | 1.16 | 0.83 | 2.5 | 2.25 | 1.43 | 64% |
| F (µg/ $cm^2 \cdot h$) | 1.73 | 8.66 | 10.1 | 3.94 | 6.11 | 3.4 | 56% |
| Q/n (µg/C) | 15.55 | 20.1 | 16.75 | 19.7 | 18.02 | 2.1 | 10.7% |
| Test 1d | Iontophoresis over 6 hours - Ag/AgCl electrodes with 2 C of AgCl | | | | | | |
| Q (µg) | 33.1 | 39.4 | 35 | 37.4 | 36.22 | 2.38 | 6.6% |
| Length of activity (h) | 4.83 | 2.5 | 2.75 | 2.25 | 3.08 | 1.03 | 33% |
| F (µg/ $cm^2 \cdot h$) | 3.42 | 7.88 | 6.36 | 8.31 | 6.49 | 1.92 | 29.5% |
| Q/n (µg/C) | 16.55 | 19.7 | 17.5 | 18.7 | 18.11 | 1.19 | 6.6% |
| Test 1e | Iontophoresis over 6 hours - Ag/AgCl electrodes with 4 C of AgCl | | | | | | |
| Q (µg) | 80.7 | 67.9 | 74.5 | 66.3 | 72.35 | 7.01 | 7.9% |
| Length of activity (h) | 4.41 | 5.5 | 2.66 | 6 | 4.65 | 1.28 | 7.9% |
| F (µg/ $cm^2 \cdot h$) | 9.15 | 6.17 | 12.05 | 5.53 | 8.21 | 2.59 | 31.4% |
| Q/n (µg/C) | 20.18 | 17 | 18.6 | 16.6 | 18.1 | 1.43 | 7.9% |

EXAMPLE 2

Study of the transdermic passage of sodium valproate (sodium isooctanoate)

The operations were carried out in iontophoresis cells each having a structure identical to that of the cells used in Example 1. In each cell, the donor compartment was filled with an aqueous solution of 5% by weight sodium valproate, 500 ppm of $NaN_3$ was added to the said solution as a bactericidal agent, while the receiver compartment or back electrode compartment was filled with the same liquid as that used in Example 1. At its end opposite the receiver compartment, the donor compartment was fitted with an electrode consisting of a previously chloridised silver film of 25 µm thickness and of 2 $cm^2$ of active surface area, the chloridisation being effected as indicated in Example 1, while the back electrode compartment was fitted with a 2 $cm^2$ electrode made of slightly chloridised silver (quantity of silver chloride corresponding to 0.1 coulomb/$cm^2$), the chloridised face of each electrode being turned towards the rat-skin membrane side.

The samples of rat skin were prepared as indicated in Example 1.

For each of the tests carried out, four identical iontophoresis cells (cells A, B, C and D) were set in operation simultaneously. The effective exchange area was 2 $cm^2$ for each skin.

A pulsed current generator made it possible simultaneously to set up between the electrodes of the four cells mounted in parallel, an electric signal of the potentiometric type having a peak voltage equal to 2 volts with a duty ratio of 70% and a frequency of 10 kHz. A resistance of 100 ohms was connected in series in the circuit.

Following the voltage at the terminals of this resistor made it possible to determine the instant from which the silver chloride had been completely consumed, the said instant being indicated by a sharp drop in the said voltage.

The pulsed current generated by the generator was applied for 6 hours, the electrode of the donor compartment of each cell containing the sodium valproate being connected to the negative pole of the said generator and the back electrodes of the cells to the positive pole.

At the end of the said duration, the medium contained in the receiver compartment of each cell was sampled and the quantity of sodium valproate which had passed through the skin separating the donor and receiver compartments of each cell was determined by assay.

Four tests 2a to 2d were carried out as follows:

Test 2a : No current was applied to the electrodes, in order to determine the passive transcutaneous diffusion over 6 hours.

Test 2b : The silver chloride electrode present in the donor compartment of each cell held a quantity of AgCl corresponding to 30 coulombs, that is to say very much greater than the quantity capable of being consumed during the running time (6 hours) of the iontophoresis operation (non-limiting electrode).

Tests 2c and 2d : The chloridised silver electrode present in the donor compartment of each cell held a quantity of AgCl corresponding respectively to 6 coulombs (test 2c) and 12 coulombs (test 2d), that is to say less than the quantity capable of being consumed during the running time (6 hours) of the iontophoresis operation (limiting electrode).

For each of the tests, a determination was made for each cell of:

the total quantity Q of valproate which had diffused in 6 hours into the receiver compartment;

the length of reversibility of the electrode of the donor compartment, that is to say the length of the iontophoresis operation in the case of tests 2a and 2b without a limiting electrode or alternatively the length of time at the end of which the silver chloride of the limiting electrode was consumed in the case of tests 2c and 2d with a limiting electrode;

the flux F representing the quantity Q divided by the length of activity and by the surface area of the electrode; and the ratio Q/n of the quantity Q to the quantity of silver chloride consumed, this latter quantity being expressed in coulombs.

The results obtained are given in Table II.

TABLE II

| | Cell A | Cell B | Cell C | Cell D | Mean | Standard deviation | % variation |
|---|---|---|---|---|---|---|---|
| Test 2a | Passive transcutaneous diffusion over 6 hours | | | | | | |
| Q (µg) | 160 | 764 | 518 | 836 | 569 | 264 | 46.4% |

TABLE II-continued

|  | Cell A | Cell B | Cell C | Cell D | Mean | Standard deviation | % variation |
|---|---|---|---|---|---|---|---|
| F ($\mu g/cm^2 \cdot h$) | 13.3 | 63.6 | 43 | 69.7 | 47.4 | 22 | 46.4% |
| Test 2b | | | Iontophoresis over 6 hours - non-limiting reversible electrodes | | | | |
| Q ($\mu g$) | 1533 | 933 | 3118 | 2988 | 2170 | 964 | 44% |
| F ($\mu g/cm^2 \cdot h$) | 128.5 | 77.6 | 267 | 248 | 182 | 78.8 | 44% |
| Test 2c | | | Iontophoresis over 6 hours - Ag/AgCl electrodes with 6 C AgCl | | | | |
| Q ($\mu g$) | 1127 | 1152 | 994 | 1000 | 1068 | 71.8 | 6.7% |
| Length of activity (h) | 1.75 | 2.75 | 3.16 | 2.5 | 2.55 | 0.75 | 24% |
| F ($\mu g/cm^2 \cdot h$) | 322 | 209 | 157 | 200 | 222 | 61 | 28% |
| Q/n ($\mu g/C$) | 188 | 192 | 165 | 166 | 178 | 12.1 | 6.8% |
| Test 2d | | | Iontophoresis over 6 hours - Ag/AgCl electrodes with 12 C AgCl | | | | |
| Q ($\mu g$) | 2273 | 2158 | 2242 | 2350 | 2256 | 68.8 | 3.0% |
| Length of activity (h) | 2.75 | 3.5 | 3.33 | 4.25 | 3.46 | 0.53 | 15.5% |
| F ($\mu g/cm^2 \cdot h$) | 413 | 308 | 337 | 267 | 333 | 50.6 | 15% |
| Q/n ($\mu g/C$) | 189 | 180 | 187 | 196 | 188 | 6 | 3.0% |

Reading the results obtained in Examples 1 and 2 and given respectively in Tables I and II clearly shows that the fluxes as well as the quantities diffused by passive means (Table I, test 1a and Table II, test 2a) are not very reproducible, as is shown by their percentage variations which go from 46.4 to 50%. The same is true for the quantities diffused by iontophoresis using non-limiting electrodes, when a constant-peak voltage signal is applied to the electrodes for an identical period of time (Table I, test 1b and Table II, test 2b). This is essentially due to the high variation in the structure of the skin, which leads to passive diffusions and impedances which are very different from one individual to another.

Reading the results obtained according to the invention (Table I, tests 1c to 1e and Table II, tests 2c to 2d) demonstrate that, despite iontophoretic currents which vary widely from one experiment to another as is indicated by the widely varying lengths of utilisation of the reversible electrodes with the same faradic capacity (that is to say holding the same quantity of AgCl), the total quantities of active principle delivered in 6 hours are directly proportional to the charge of the electrodes, that is to say, in fact, to the total quantity of current consumed by the system, and with a percentage variation which is 5 to 10 times less than with the conventional methods. This signifies that the electrical efficiencies, that is to say the ratios of the quantities of active principle which have diffused to the quantities of current which have been used in the iontophoresis process (Q/n), are quite reproducible.

The limiting electrodes according to the invention behave like chemical counters capable of limiting the total quantity of current which has been administered and of leading, without any complicated and/or costly electronic device, to a total cutting of or at the very least a considerable decrease in the current when the predetermined quantity of current, corresponding to the given total quantity of active principle to be administered, has been reached.

It should furthermore be noted that this effect was obtained by applying between the electrodes, and therefore to the skin, constant-peak voltages which are particularly easy to obtain whether they are continuous or pulsed. This approach is the safest one because it prevents, when the voltages applied are suitably chosen, any secondary reaction of oxidation or reduction of the active principle, of the surrounding medium or of the skin, which could lead to the appearance of toxic or poorly tolerated secondary products.

In order to obtain the same control of the quantity of current distributed by the devices whose electrode capacity is not adjusted (Example 1, test 1b and Example 2, test 2b), it would be necessary to install either a device (coulometer) for counting the quantity of current delivered by the device with set voltage or strictly to control the length of application of the treatment when the device supplies a constant-intensity current. In the first case, the electronic device is costly and difficult to produce, especially in the case of pulsed currents, but is less dangerous since in the second case, poor contacts or an abnormally high impedance of certain subjects may lead to the voltage reached by the device rising excessively and becoming dangerous either from the point of view of cutaneous tolerance or through the appearance of uncontrolled reactions destroying the active principle or active principles. It is therefore indispensable to incorporate into such devices, in addition to the timer switch, a device limiting the voltage at the electrodes, whence an additional cost combined with a risk of lower reliability.

EXAMPLE 3

Study of the transdermic passage of sodium valoroate with a limiting back electrode based on aluminium The operations were carried out in iontophoresis cells each having a structure identical to that of the cells used in Example 1. In each cell, the donor compartment (cathodic compartment) was filled with a 10% by weight aqueous solution of sodium valproate, 500 ppm of $NaN_3$ being added to the said solution as a biocide.

The receiver or back electrode compartment (anodic compartment) was filled with physiological salt solution buffered to pH 7. At its end opposite the receiver compartment, the donor compartment was fitted with a chloridised silver electrode having an active surface area of 2 cm² and holding a quantity of AgCl corresponding to 4 coulombs/cm². The back electrode compartment was fitted with a 2 cm² electrode cut out from a sheet of polypropylene coated with an aluminium deposit of thickness equal to 200 nm, this aluminised polypropylene sheet being a commercial product. The quantity of aluminium present on the back electrode corresponded to 0.6 coulombs/cm². Contact was made with clamps having jaws disposed on a part of the metal coating previously covered with an electronically conducting varnish of the silver epoxide type. The chloridised face of the electrode of the donor compartment and the aluminium deposit of the limiting electrode of the receiver compartment were turned towards the rat-skin membrane side.

The samples of rat skin were prepared as indicated in Example 1.

In this example, four identical iontophoresis cells (cells A, B, C and D) were used. The effective exchange surface was 2 cm² for each skin.

Using an apparatus marketed under the name PHORESOR ®, a direct current was set at the electrodes of each of the four iontophoresis cells, having a constant intensity whatever the voltage which this set intensity creates between the anode and the cathode of each cell, the said set intensity being equal to 0.6 mA (current density equal to 0.3 mA/cm²).

A coulometer, mounted in the electric circuit of the cell, directly measured in coulombs the quantity of direct current which had passed through the whole of the circuit, while a voltmeter, mounted in parallel, indicated the value of the voltage between the anode and the cathode of the cell.

The current was applied so that the electrode of the donor compartment of each cell containing the sodium valproate was connected to the negative pole of the associated current generator and the back electrode of the cell to the positive pole of the said generator.

After it was started up, each cell operated until the cutting of the current triggered by the total consumption of the aluminium anode deposited on the polypropylene film. Six hours after start-up, the medium contained in the receiver compartment of each cell was sampled and the quantity of sodium valproate which had passed through the skin separating the donor and receiver compartments of each cell was determined by assay.

For each of the cells, the following values were determined:

quantity of current K read from the coulometer fitted to the electric circuit of the cell;

mean voltage V measured between the electrodes of the cell;

time t elapsed between the start-up of the experiment and the cutting of the current triggered by the total consumption of the aluminium of the anode;

total quantity Q of valproate which had diffused into the receiver compartment during the experiment; and ratio Q/K of the quantity Q to the quantity of current K expressing in coulombs the quantity of aluminium consumed.

The results obtained are given in Table III.

TABLE III

| | K (coulomb) | V (volts) | t (s) | Q (µg) | Q/K (µC) |
|---|---|---|---|---|---|
| Cell A | 1.296 | 0.93 | 2160 | 336 | 259 |
| Cell B | 1.332 | 2.48 | 2220 | 352 | 264 |
| Cell C | 1.116 | 3.3 | 1860 | 307 | 275 |
| Cell D | 1.080 | 1.78 | 1800 | 268 | 248 |
| Mean | 1.210 | 2.12 | 2010 | 316 | 261.5 |
| Standard deviation | 1.110 | 0.87 | 3.04 | 32 | 9.7 |
| % variation | 9.1% | 41% | 9.1% | 10% | 3.7% |

Reading the results recorded in Table III leads to the following remarks:

all the electrodes based on aluminium were cut out from the same sample of aluminised polypropylene sheet and were seen to have very similar coulombic capacities, which shows that, against all expectation, this quality of aluminised polypropylene sheet allows consumption of the whole of the aluminium deposit from the face in contact with the electrolyte;

the duration of the experiments is quite reproducible, which demonstrates that the electrode has indeed functioned as an electrochemical counter of the quantity of current consumed;

significant deviations were observed in the voltages measured between the electrodes. These deviations are due to significant differences in impedance of the skin from one test to another. It will be understood that these voltages can in certain cases reach values such that they are poorly tolerated or they lead to undesirable secondary reactions if higher currents were set or the contacts between the skin and the reservoir of active principle and/or the electrode associated with the active principle were defective;

despite these significant variations in voltage, the quantities of active principle which have passed through the skin during each experiment are quite reproducible and perfectly correlated with the capacity of each limiting electrode;

the limiting electrodes, that is to say with controlled coulombic capacity, based on aluminium therefore functioned successfully as a timer counter in this case of an intensiostatic set-up and did so with complete safety and without an electronic or mechanical apparatus which could increase the cost of the devices and make them heavier if they are intended to be carried on the skin itself by potential users.

EXAMPLE 4

Study of the transdermic passage of sodium valoroate with a limiting back electrode based on aluminium and set pulsed voltage The operations were carried out in iontophoresis cells each having a structure identical to that of the cells used in Example 1. In each cell, the donor compartment (cathodic compartment) was filled with a 10% by weight aqueous solution of sodium valproate, 500 ppm of NaN₃ being added to the said solution as a bactericidal agent, while the receiver compartment or back electrode compartment was filled with physiological salt solution buffered to pH 7. At its end opposite the receiver compartment, the donor compartment was fitted with a chloridised silver electrode having an active surface area of 2 cm² and holding a quantity of silver chloride corresponding to 4 coulombs cm². The back electrode compartment was fitted with a 2 cm² electrode cut out from a sheet of polypropylene coated with an aluminium deposit of thickness equal to 200 nm, the quantity of aluminium present on the back electrode corresponding to 0.6 coulomb/cm². Contact was made using clamps with jaws disposed on a part of the metal coating covered with an electronically conducting varnish of the silver epoxide type. The chloridised face of the electrode of the donor compartment and the aluminium deposit of the limiting electrode of the receiver compartment being turned towards the rat-skin membrane side.

The samples of rat skin were prepared as indicated in Example 1.

In producing this example, four identical iontophoresis cells (cells A, B, C and D) were started up simultaneously. The effective exchange surface was 2 cm² for each skin.

A pulsed-current generator made it possible simultaneously to establish between the electrodes of the four cells mounted in parallel, an electric signal of the potentiometric type having a peak voltage equal to 3 volts, with a duty ratio of 50% and a frequency of 30 kHz. A resistance of 100 ohms was connected in series in the circuit.

Following the voltage at the terminals of this resistor made it possible to determine the instant from which the aluminium of the limiting electrode was completely consumed, the said instant being indicated by a sharp drop in the said voltage.

The pulsed current supplied by the generator was applied for 6 hours, the electrode of the donor compartment of each cell containing the sodium valproate being connected to the negative pole of the said generator and the back electrodes of the cells to the positive pole.

At the end of the said time, the medium contained in the receiver compartment of each cell was sampled and the quantity of sodium valproate which had passed through the skin separating the donor and receiver compartments of each cell was determined by assay.

For each of the cells, the following values were determined:

total quantity Q of valproate which had diffused in 6 hours (duration of the experiment) into the receiver compartment;

duration t during which the current has a value signifying iontophoresis, that is to say the duration at the end of which the aluminium of the back electrode has been completely consumed;

flux F representing the quantity Q divided by the duration t and by the surface area of the electrode;

ratio Q/n of the quantity Q to the quantity of aluminium consumed, this latter quantity being expressed in coulombs and taken to be equal to 1.21 (mean value found in Example 3).

The results obtained ar recorded in Table IV.

TABLE IV

|  | Q (μg) | t (min) | F (μg/cm²·h) | Q/n (μg/C) |
|---|---|---|---|---|
| Cell A | 327 | 40 | 245.5 | 270.2 |
| Cell B | 321 | 55 | 175.1 | 265.3 |
| Cell C | 295 | 60 | 147.5 | 243.8 |
| Cell D | 301 | 72 | 125.4 | 248.8 |
| Mean | 311 | 56.75 | 173.4 | 257 |
| Standard deviation | 13 | 11.5 | 45 | 11 |
| % variation | 4.3% | 20.2% | 26% | 4.3% |

Reading the results presented in Table IV leads to the following conclusions:

the duration of the experiments is highly variable and obviously depends on the impedance of each sample of skin;

the transdermic fluxes F are highly variable from one experiment to another;

despite widely different durations t of activity of the signal, it is possible to see that the quantities Q delivered as well as the ratios Q/n are highly reproducible as shown by the small standard deviations corresponding to the values of Q and Q/n;

the ratios Q/n are of the same order of magnitude as the ratios Q/K in Example 3 although the currents applied are completely different.

EXAMPLE 5

Study of the transdermic passage of sodium valproate with a limiting back electrode based on aluminium and a set continuous voltage The operations were carried out as described in Example 4 with, however, the following changes:

the aqueous solution of sodium valproate held 15% by weight of this compound;

the back electrode was cut out from a sheet of aluminised polypropylene whose coating was enriched in aluminium by sputtering of aluminium under vacuum, the said back electrode having a thickness of aluminium equal to 400 nm; and the pulsed current generator was replaced by a direct current generator delivering a continuous voltage equal to 1.5 volts, a coulometer and a milliammeter were mounted in series with each iontophoresis cell.

For each of the four cells A, B, C and D, the following values were determined:

total quantity Q of valproate which had diffused during the duration of the experiment (6 hours) into the receiver compartment;

duration t during which the current has a value signifying iontophoresis, that is to say the duration at the end of which the aluminium of the back electrode has been completely consumed;

quantity of current K read from the coulometer at the end of the duration t;

mean intensity I of the current read from the milliammeter;

flux F representing the quantity Q divided by the duration t and by the surface area of the electrode; and ratio Q/K of the quantity Q to the quantity K expressing in coulombs the quantity of aluminium consumed.

The results obtained are given in Table V.

TABLE V

|  | K (coulombs) | Q (μg) | t (h) | F (μg/cm²·h) | Q/K (μg/C) | I (mA) |
|---|---|---|---|---|---|---|
| Cell A | 2.92 | 814 | 3.08 | 132 | 279 | 0.133 |
| Cell B | 2.64 | 745 | 1.75 | 212.8 | 282 | 0.208 |
| Cell C | 2.42 | 718 | 2.08 | 186.7 | 297 | 0.160 |
| Cell D | 2.74 | 843 | 1.08 | 389.1 | 307 | 0.351 |
| Mean | 2.68 | 795 | 2 | 230.1 | 292 | 0.213 |
| Standard deviation | 0.18 | 36.9 | 0.72 | 96.3 | 11.7 | 0.084 |
| % variation | 6.7 | 4.6 | 36 | 41.8 | 4.0 | 39.5 |

Reading the results which figure in Table V leads to the following conclusions:

at constant voltage, which is the only way of avoiding harmful secondary oxidation-reduction reactions, the intensities and the durations of passing the current vary widely from one experiment to another;

the total quantities of active principle which had diffused through the skin are, conversely, highly reproducible;

the quantities which had diffused per coulomb are in this example slightly greater than those determined for Examples 3 and 4, because in the present example the concentration of active principle (sodium valproate) in the donor compartment was higher.

As a conclusion for the examples presented, whether the electric signal is pulsed or continuous, whether it has set peak voltage or set intensity, the use of limiting electrodes in the system, as the invention proposes, makes it possible better to control the quantities of active principle delivered through the skin and to do this in a reliable manner which prevents any excess of active principle being administered and without an electronic device other than that which produces the iontophoretic electric signal.

We claim:

1. Iontophoresis device for transcutaneous administration of a given total quantity of an active principle to a subject comprising:
   a first electrode assembly including a first electrode called the active electrode, in contact with a reservoir element for holding an electrolyte containing the active principle and for contacting an area of the skin of the subject to achieve ionic conducting continuity between the active electrode and the said area,
   a second electrode assembly including a second electrode called the back electrode of opposite polarity to that associated with the active principle, in contact with a receptor element for contacting a portion of the skin of the subject to achieve ionic conducting continuity between the second electrode and the said portion, and
   an electric signal generator connected to the two electrodes, wherein one of said first electrode assembly and said second electrode assembly further comprises a limiting consumable electrode formed of a limited quantity of electrochemically consumable material, said limited quantity being chosen such that the quantity of electricity necessary for its electrochemical consumption corresponds of the quantity of electricity necessary for administering the given total quantity of active principle to the subject said limiting consumable electrode being disposed in one of said first and second electrode assemblies such that the flow of current between the two electrodes is broken when the electrochemically consumable material has been consumed.

2. Device according to claim 1, wherein the quantity of active principle present in the reservoir element at the start of the operation is in excess by approximately 2% to 1000% with respect to the given total quantity of active principle to be administered.

3. Device according to claim 1 wherein the active electrode is the limiting consumable electrode, while the back electrode is an electrode which is not electrochemically consumable.

4. Device according to claim 3, wherein the limiting consumable electrode is used as the anode, the electrochemically consumable material of the said electrode being chosen from materials which are consumable by electrochemical oxidation.

5. Device according to claim 4, wherein the limiting consumable electrode is used as the anode and is comprised of at least one metal selected from the group consisting of Al, Ag, Cu, Mg and Zn deposited on an insulating support or on an electronically conducting support selected from the group consisting of titanium, stainless steel, platinum, carbon, graphite and a conducting polymer.

6. Device according to claim 3, wherein the limiting consumable electrode is used as the cathode, the electrochemically consumable material of the said electrode being selected from ionisable metal compounds whose metal ions are capable of being reduced electrochemically into the corresponding metal.

7. Device according to claim 6, wherein the limiting consumable electrode is used as the cathode, said electrode being based on AgCl or CuCl deposited on a copper, silver, stainless steel, titanium, carbon, polypropylene, polyethylene or conducting polymer support.

8. The device according to claim 3, wherein the limiting consumable electrode is used as the anode, the electrochemically consumable material of said electrode being comprised of at least one metal elected from the group consisting of Al, Cu, Mg, Zn and Ag.

9. The device according to claim 3, wherein the limiting consumable electrode is used as the cathode, the electrochemically consumable material of said electrode being at least one of AgCl and CuCl.

10. Device according to claim 1 wherein the active electrode is an electrode which is not electrochemically consumable, while the back electrode is the limiting consumable electrode.

11. Device according to claim 1 wherein the active electrode and the back electrode are both electrochemically consumable electrodes, one of the electrodes being the limiting consumable electrode, while the other electrode is a non-limiting consumable electrode, that is to say holding an electrochemically consumable material in a quantity in excess with respect to the quantity which would be consumed by the passage of the quantity of electricity consuming the quantity of electrochemically consumable material of the limiting consumable electrode.

12. The device according to claim 11, wherein the non-limiting consumable electrode is used as the anode, the electrochemically consumable material of said electrode being chosen from materials which are consumable by electrochemical oxidation.

13. The device according to claim 11, herein the non-limiting consumable electrode is used as the anode, the electrochemically consumable material of said electrode being comprised of at least one metal selected from the group consisting of Al, Cu, Mg, Zn and Ag.

14. The device according to claim 11, wherein the non-limiting consumable electrode is used as the cathode, the electrochemically consumable material of said electrode being chosen from ionisable metal compounds whose metal ions are capable of being reduced electrochemically into the corresponding metal.

15. The device according to claim 11, wherein the non-limiting consumable electrode is used as the cathode, the electrochemically consumable material of said electrode being at least one of AgCl and CuCl.

16. The device according to claim 11, wherein the non-limiting consumable electrode is used as the cathode, said electrode being comprised of AgCl or CuCl deposited on a copper, silver, stainless steel, titanium, carbon, polypropylene, polyethylene or conductive polymer support.

17. The device according to claim 1, wherein the active principle contained in the electrolyte is in at least partially ionised form and said active electrode has the same polarity as the ions of the active principle.

18. The device according to claim 1, wherein the active principle contained in the electrolyte is in neutral form and said active electrode has a positive polarity.

19. The device according to claim 1, wherein said receptor element holds an indifferent electrolyte.

20. The device according to claim 1, wherein said consumable electrode consists of an electrochemically consumable material associated with an insulating support.

21. The device according to claim 20, wherein said electronically conducting support is made of material having a hydrogen overpotential in the presence of said electrolyte at least equal to that of aluminum.

22. The device according to claim 20, wherein said electronically conducting support is made of material which is not consumable by electrochemical oxidation.

23. The device according to claim 1, wherein said consumable electrode consists of an electrochemically consumable material associated with an electronically conducting support made of a material which resists corrosion by the electrolyte associated with the electrode in the absence of a current.

24. The device according to claim 1, wherein the active principle is present in the reservoir element at the start of operation in a quantity greater than the total quantity to be administered to the subject.

25. The device according to claim 1, wherein the quantity of active principle present in the reservoir element at the start of the operation is in excess by about 2% to 500% with respect to the given total quantity of active principle to be administered.

26. Iontophoresis device for transcutaneous administration of a given total quantity of an active principle to a subject, which comprises:
 a) a first electrode assembly consisting of a first electrode, called the active electrode, in contact with a reservoir element for holding an electrolyte containing the active principle in an at least partially ionised form or in a neutral form and for providing, when it is placed in contact with an area of the skin of the subject, ionic conducting continuity between said first electrode and said area, said first electrode having the same polarity as the ions of the active principle or a positive polarity if the active principle is neutral and the active principle being present, at the start of the operation, in the reservoir element holding it in a quantity greater than the given total quantity to be administered to the subject,
 b) a second electrode assembly selected from the group consisting of i) a second electrode, called the back electrode, of opposite polarity to that associated with the active principle and ii) a second electrode of said type i) in contact with a receptor element holding an indifferent electrolyte, said receptor element being arranged to provide, when it is placed in contact with a portion of the skin of the subject, ionic conducting continuity between the second electrode and said portion, and
 c) an electric signal generator for connecting to the active and back electrodes and for applying between said electrodes an intensiometric signal comprising a signal of set average intensity or a potentiometric signal comprising a signal of set average voltage, the said signal being continuous or pulsed and permanent or intermittent, with or without temporary polarity inversion and having a frequency ranging from 0 to 500 kHz;
 and wherein
  at least one of the first electrode in contact with the reservoir element and the second electrode in contact with the receptor elements further comprising a consumable electrode formed of an electrochemically consumable material associated with an insulating support or with an electronically conducting support, said electronically conducting support being made of a material which resists corrosion by the electrolyte associated with the electrode in the absence of a current and which has, when the consumable electrode is a negative electrode, a hydrogen overpotential in the presence of said electrolyte at least equal to that of aluminum or which is not consumable by electrochemical oxidation when the consumable electrode is a positive electrode, and
  the consumable electrode or one of the consumable electrodes holds a limited quantity of the electrochemically consumable material associated with the support said limited quantity being chosen so that the quantity of electricity necessary for its electrochemical consumption corresponds to the quantity of electricity necessary for administering the given total quantity of active principle to the subject, so that the flow of the current between the electrodes is practically broken when the consumable material of the electrode carrying the limited quantity of consumable material has been consumed.

27. The device according to claim 26, wherein the electric signal is a pulsed signal having a ratio between the duration of the elementary pulse, whose repetition forms the pulsed signal, and the time interval separating two successive appearances of this pulse, called a duty ratio, ranging from 0.05 to 0.95.

28. The device according to claim 27, wherein said duty ratio ranges from 0.1 to 0.8.

29. The device according to claim 26, wherein the electric signal applied between the active electrode and the back electrode is of the potentiometric type and has an average voltage between 0.1 and 50 volts so that the density of the average current generated between said electrodes has a value less than 5 mA/cm$^2$.

30. The device according to claim 26, wherein said frequency ranges from 0 to 100 kHz.

31. The device according to claim 26, wherein the electric signal applied between the active electrode and the back electrode is of the potentiometric type and has an average voltage between 0.5 and 20 volts so that the density of the average current generated between said electrodes has a value less than 5 mA/cm$^2$.

32. The device according to claim 31, wherein the density of the average current generated between the active and back electrodes has a value at most equal to 1 mA/cm$^2$.

33. The device according to claim 32, wherein the density of the average current generated between the active and back electrodes has a value between 0.03 and 0.5 mA/cm$^2$.

* * * * *